US012188589B2

(12) United States Patent
Knierim

(10) Patent No.: US 12,188,589 B2
(45) Date of Patent: Jan. 7, 2025

(54) ANCHORING DEVICE FOR ANCHORING A FLEXIBLE LINE AS WELL AS A CORRESPONDING SYSTEM

(71) Applicant: B. Braun Avitum AG, Melsungen (DE)

(72) Inventor: Michael Knierim, Melsungen-Schwarzenberg (DE)

(73) Assignee: B. Braun Avitum AG, Melsungen (DE)

( * ) Notice: Subject to any disclaimer, the term of this patent is extended or adjusted under 35 U.S.C. 154(b) by 0 days.

(21) Appl. No.: 18/140,453

(22) Filed: Apr. 27, 2023

(65) Prior Publication Data
US 2023/0349490 A1   Nov. 2, 2023

(30) Foreign Application Priority Data
Apr. 29, 2022   (DE) ...................... 10 2022 110 565.2

(51) Int. Cl.
*F16L 3/10*   (2006.01)
(52) U.S. Cl.
CPC .................................. *F16L 3/1075* (2013.01)
(58) Field of Classification Search
CPC ....... F16L 5/14; F16L 3/26; F16L 3/10; F16L 3/1033; F16L 3/1226; F16L 3/1075; H02G 15/007; H02G 3/0633; H02G 3/32; A61M 5/1418; A61M 2025/024; A61M 25/02
USPC .................................................. 248/49–74.5
See application file for complete search history.

(56) References Cited

U.S. PATENT DOCUMENTS

| | | | |
|---|---|---|---|
| 2,895,003 A | | 7/1959 | Rapata |
| 4,403,712 A | * | 9/1983 | Wiesinger ................. E05D 1/02 |
| | | | 220/838 |
| 4,845,316 A | * | 7/1989 | Kaercher ............. H02G 3/0633 |
| | | | 248/68.1 |

(Continued)

FOREIGN PATENT DOCUMENTS

| | | |
|---|---|---|
| DE | 102015213686 A1 | 1/2017 |
| EP | 1265668 B1 | 11/2006 |
| EP | 3714920 A1 | 9/2020 |

OTHER PUBLICATIONS

Search Report received in German Application No. 10 2022 110 565.2 dated Mar. 17, 2023, with translation, 7 pages.

(Continued)

*Primary Examiner* — Christopher Garft
(74) *Attorney, Agent, or Firm* — Christopher A. Rothe; CM Law

(57) ABSTRACT

A device for anchoring a flexible line includes a base having an indentation that receives a portion of the line and a cover. The base defines a cavity curved at a first site in a first direction to prevent or limit the line from sliding out of the indentation. The cover releases the indentation for insertion of the line when the cover is in an open position, and covers the indentation when in a closed position to prevent or limit the received portion of the line from sliding out of the indentation. The cover has a receptacle portion which, in a closed position, is arranged at one end of the indentation and extends the cavity so that the cavity is curved in a region of the receptacle portion at a second site in a second direction running transversely or in a direction opposite to the first direction.

12 Claims, 3 Drawing Sheets

(56) References Cited

U.S. PATENT DOCUMENTS

| | | | | |
|---|---|---|---|---|
| 5,323,992 | A * | 6/1994 | Sifers | F16L 3/04 |
| | | | | 248/65 |
| 5,556,059 | A * | 9/1996 | Maeda | B60R 16/0215 |
| | | | | 174/72 A |
| 6,387,076 | B1 | 5/2002 | Landuyt | |
| 7,487,791 | B1 * | 2/2009 | Bradley | B65H 75/362 |
| | | | | 137/355.16 |
| 11,273,773 | B2 * | 3/2022 | Fujimura | H02G 3/0418 |
| 2012/0162869 | A1 * | 6/2012 | Li | H05K 5/0247 |
| | | | | 361/679.01 |
| 2015/0101837 | A1 * | 4/2015 | Evangelista | H02G 15/113 |
| | | | | 29/525 |
| 2019/0022303 | A1 * | 1/2019 | Headlee | A61M 5/1418 |

OTHER PUBLICATIONS

Search Report received in European Application No. 23169811.9-1122 dated Nov. 16, 2023, with translation, 12 pages.

* cited by examiner

ANCHORING DEVICE FOR ANCHORING A FLEXIBLE LINE AS WELL AS A CORRESPONDING SYSTEM

CROSS-REFERENCE TO RELATED APPLICATION(S)

This application claims priority under 35 U.S.C. § 119 to German Application No. 10 2022 110 565.2, filed Apr. 29, 2022, the content of which is incorporated by reference herein in its entirety.

FIELD

The present disclosure relates to an anchoring device for anchoring a flexible line, preferably an electric cable and/or a tube configured for transporting substances/media, to a medical device or to a person to be treated and/or monitored. Furthermore, the present disclosure relates to a system comprising an anchoring device according to the disclosure and a line.

BACKGROUND

EP 1 265 668 B1 discloses an anchoring device for anchoring a flexible line with a base having an indentation defining a curvilinear cavity which is curved at three sites so as to be able to grip a part of the line received in the indentation and to prevent or complicate in a self-locking manner that the part of the line received in the indentation slides out in the extension direction of the indentation. Furthermore, the known anchoring device comprises a cover which, in an opened position, releases the indentation for insertion of the line and, in a closed position, covers the indentation in order to be able to prevent or complicate that the part of the line received in the indentation slides out transversely to the extension direction of the indentation.

The problem with the anchoring device according to EP 1 265 668 B1 is that inserting a line into the indentation may be complicated due to the curvilinear shape of the cavity.

SUMMARY

The object of the present disclosure, therefore, is to provide an anchoring device configured to facilitate installation of a line to the anchoring device without necessarily degrading the anchoring of the line.

An anchoring device according to the disclosure is suitable for anchoring a flexible line, in particular an electric cable and/or a tube configured for transporting substances/media, in particular to a medical device or to a person to be treated and/or monitored, preferably optionally to a medical device or to a person to be treated and/or monitored.

The anchoring device comprises a base and a cover.

The base comprises an indentation adapted to receive a portion of the line therein and defining a curvilinear cavity curved at a first site in a first direction to prevent or complicate in a self-locking manner sliding of the portion of the line received in the indentation (out of the indentation) in the extension direction of the indentation.

The indentation defines the curvilinear cavity in that surfaces of the indentation are shaped and/or arranged in such a way that they are tangential to outer surfaces of the part of the line received in the indentation and can therefore be in surface contact with the part of the line received in the indentation (defined wrap angle). In other words, the indentation is configured in such a way that the part of the line received in the indentation has a curvilinear shape due to surface contact with surfaces of the indentation.

In an opened position (of the cover relative to the base), the cover releases the indentation for insertion of the line, and in a closed position (of the cover relative to the base), the cover covers the indentation in order to prevent or complicate sliding out of the part of the line received in the indentation (out of the indentation) transversely to the extension direction of the indentation.

According to the disclosure, the cover has a receptacle portion which, in the closed position of the cover, is arranged at one end of the indentation and which extends the curvilinear cavity defined by the indentation in such a way that the latter is curved in the region of the receptacle portion at a second site in a second direction running transversely or in the opposite direction to the first direction.

In other words, the anchoring device is configured in such a way that in the opened position of the cover (relative to the base) sliding out of the part of the line received in the indentation (out of the indentation) in the extension direction of the indentation can be prevented or complicated in a self-locking manner, i.e. frictionally, by the indentation, and in the closed position of the cover (relative to the base) sliding out of the part of the line received in the indentation (out of the indentation) in the extension direction of the indentation can be prevented or complicated in a self-locking manner, i.e. frictionally, by the indentation as well as by the receptacle portion of the cover, and sliding out of the part of the line received in the indentation (out of the indentation) transversely to the extension direction of the indentation can be prevented or complicated in a form-fitting manner by the cover. The receptacle portion is thus in particular configured to secure or respectively support the (axial) frictional connection between the anchoring device and the line caused by the indentation via a first curvature by means of a second curvature.

By providing the receptacle portion on the cover and the functional division of the frictional connection between the anchoring device and the line on the one hand into a frictional connection between the base and the line and on the other hand into a frictional connection between the cover and the line, it is advantageously possible to configure the indentation in such a simple way that insertion of the line is easy without worsening the anchoring of the line.

According to an aspect of the disclosure, the cover may include a second receptacle portion arranged at a second end of the indentation in the closed position of the cover and extending the curvilinear cavity defined by the indentation such that the cavity is curved in the region of the second receptacle portion at a third site in a third direction transverse or opposite to the first direction. In particular, the two receptacle portions may be configured such that a line received by the anchoring device at the second site and the third site is curved by the same amount.

By providing a second receptacle portion, the frictional effect of the cover can be further improved. When anchoring a tube via the second receptacle portion, it is furthermore possible to advantageously influence or at least partially compensate for a resulting impulse force caused by a fluid flowing in the tube.

According to an aspect of the disclosure, the second and third directions may run or be parallel to each other.

If the two receptacle portions are configured in such a way that a line received by the anchoring device at the second site and the third site is curved in directions parallel to each other, it is possible to make closing the cover (i.e. moving the cover from the opened position to the closed position)

ergonomically advantageous. In particular, this can be achieved if the line received by the anchoring device at the second site and the third site is curved in directions parallel to each other by the same amount.

According to an aspect of the disclosure, the base may comprise a base plate and three or more pins extending from the base plate, and the indentation may be formed by two or more spaces extending between the pins.

As used herein, a 'pin' is understood to be an elongated structure having a longitudinal extent greater than a mean transverse extent thereof.

In particular, at least one of the pins may be configured such that its free end has a greater transverse extent than adjacent regions of the pin, so that the indentation has an undercut. Preferably, two of the three pins or all three pins may be configured such that the respective free end has a greater transverse extent than adjacent regions of the corresponding pin.

By forming the indentation via pins, the indentation can be elastically configured without having to provide different materials. If pins with widened free ends are provided, it is possible to establish a clip connection with a line received in the indentation.

According to an aspect of the disclosure, the cover may be configured such that, in the closed position of the cover, at least a part of the cover abuts at least one of the pins along its longitudinal extension.

'Abutting' in this context means making surface contact.

According to an aspect of the disclosure, the cover may include at least one of the three pins of the base plate, e.g., the middle pin. In a further embodiment, the cover or a receptacle portion of a receptacle part may serve as a pin to define/fix the curvilinear cavity with the other pins of the pins extending from the base plate.

In particular, the cover may be configured in such a way that it has at least one pin which, in the closed position of the cover, abuts against one of the pins of the base. Preferably, the cover may have two pins which, in the closed position of the cover, each abut on a corresponding pin of the three pins of the base. In particular, the two pins of the cover may be configured in such a way that, in the closed position of the cover, they abut on the two outer pins of the base.

If the cover is configured in such a way that parts of it are in surface contact with the pins of the base in the closed position of the cover, it is advantageously possible to keep the stiffness of the indentation in the opened position of the cover low for easy insertion of the line and to increase the stiffness of the indentation in the closed position of the cover for holding the inserted line as compared to the opened position.

According to an aspect of the disclosure, the cover may be pivotably connected to the base via a cover hinge, and the cover hinge may be configured on the receptacle portion, in particular also on the second receptacle portion.

If the receptacle portion, which can provide at least one further curvature of a line received in the indentation, or respectively if the receptacle portions are arranged in the immediate vicinity of the cover hinge, it is possible to have the line curved in a particularly ergonomic manner.

According to an aspect of the disclosure, the cover may comprise a coupling portion pivotably connected to the remaining part of the cover via a coupling portion hinge and which is configured to be coupled to the base to be releasable without tools in the closed position of the cover and to prevent or complicate sliding out of the part of the line received in the indentation transversely to the extension direction of the indentation. In particular, the coupling portion may be configured such that the receptacle portion or the receptacle portions is/are arranged apart from the coupling portion. Preferably, the cover may be configured such that one or more pins are formed on the coupling portion. In particular, the pin or pins may be configured such that in a coupled position of the coupling portion (relative to the base), the pin or pins can interact in a form-fitting and/or friction-fitting manner with the base or with a part of the base. Preferably, the pin may be the same pin that can abut on the corresponding pin on the base or, respectively, the pins may be the same pins that can abut on the corresponding pins on the base by moving the cover to the closed position. Preferably, the base may comprise a clip or a flexible tongue, respectively, and the coupling portion of the cover may be configured to interact in a form-fitting manner with the clip or the flexible tongue in the coupled position of the coupling portion (relative to the base). The flexible tongue may also be arranged on the cover.

The formation of the pivotable coupling portion can advantageously improve the operability of the anchoring device.

In general, the function would also be possible with one hinge instead of two hinges. The advantage of two hinges is the improved connection possibility to the base. Furthermore, the material in the film hinges is subjected to less stress, since only 90 degrees of deformation take place (180 degrees with one hinge).

According to an aspect of the disclosure, a pivot axis of the coupling portion hinge with respect to which the coupling portion is pivotable relative to the remaining part of the cover may be parallel to a pivot axis of the cover hinge with respect to which the cover is pivotable relative to the base.

By orienting the pivot axis of the coupling portion hinge parallel to the pivot axis of the cover hinge, the operability of the anchoring device can be further improved.

According to an aspect of the disclosure, the base and the cover may be integrally configured and the cover hinge and the coupling portion hinge may be configured as film hinges.

If the anchoring device is integrally configured, the effort required to manufacture the anchoring device may be reduced in terms of cost and/or time.

According to an aspect of the disclosure, the base may comprise a sensor accommodation. In particular, the sensor accommodation may be configured as a cylindrical, in particular circular-cylindrical, recess.

When the anchoring device is configured with the sensor accommodation, it is possible to efficiently attach a sensor together with a strain-relieved line to a medical device or to a person to be treated and/or monitored.

The disclosure furthermore relates to a system comprising an anchoring device according to the disclosure and a corresponding line. In particular, the anchoring device may comprise a sensor accommodation. Preferably, the system may comprise a sensor.

BRIEF DESCRIPTION OF THE DRAWINGS

The present disclosure is described in more detail below based on a preferred configuration example with reference to the accompanying drawings. The following is shown.

DETAILED DESCRIPTION

Figure 1:
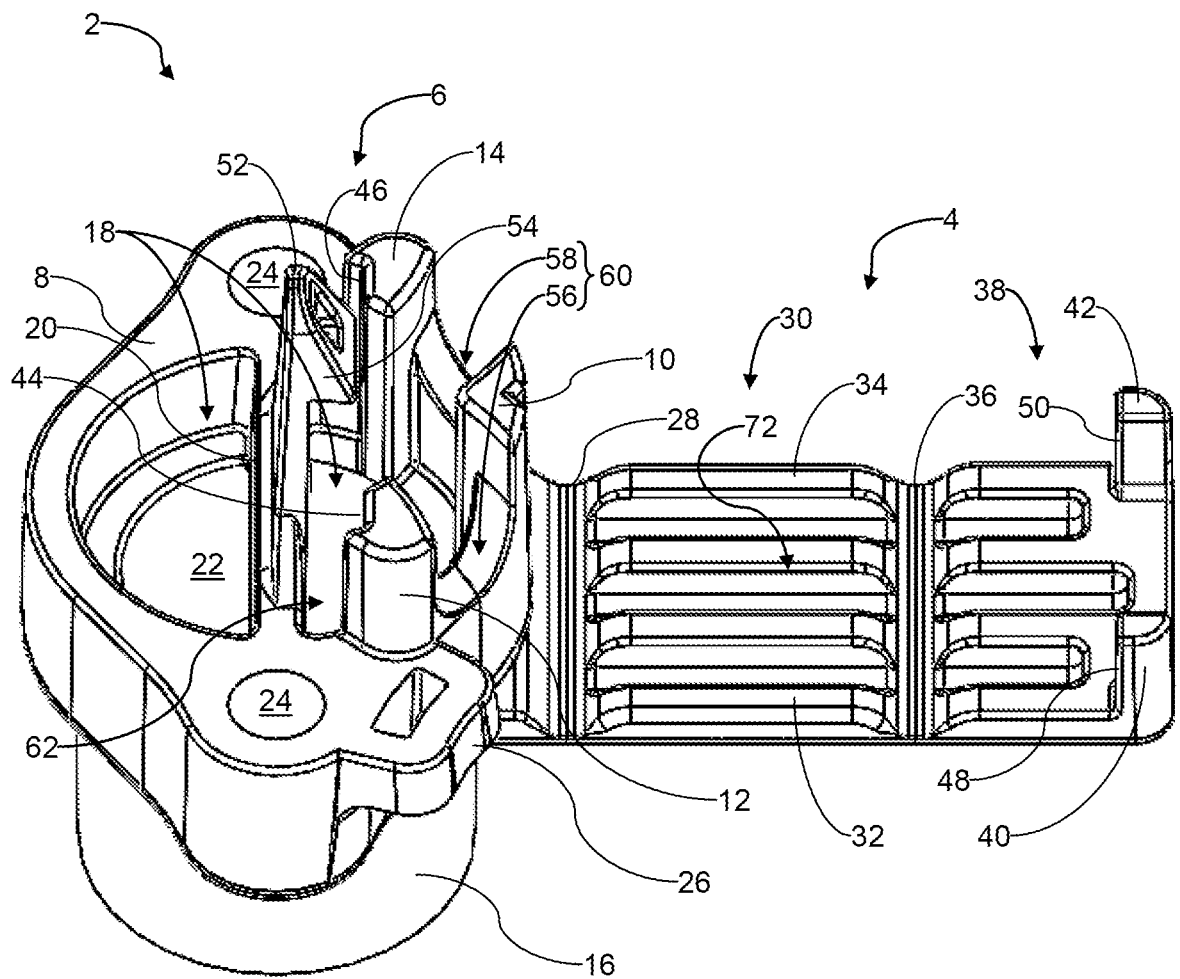
FIG. 1 shows a perspective view of an anchoring device according to the disclosure in an opened state, in which a cover is in an opened position relative to a base.

FIG. 1 shows a perspective view of an anchoring device 2 according to the disclosure in an opened state, in which a cover 4 is in an opened position relative to a base 6.

The base 6 has a base plate 8, from the top of which three pins 10, 12 and 14 extend upward. The base plate 8 has the outline of a rounded rhombus. The three pins 10, 12 and 14 are arranged in a triangle. The middle pin 10 is arranged at one corner of the rhombus-shaped base plate 8 and the two other or respectively outer pins 12 and 14 are arranged at the two sides of the rhombus-shaped base plate 8 adjacent to the corner of the middle pin 10.

A hollow-cylindrical projection 16 extends downward from the underside of the base plate 8 and is configured concentrically with the base plate 8. Two semi-circular cylindrical recesses 18 are configured in the base plate 8, whose planar sides are arranged parallel to each other such that their round sides lie in a common circular-cylindrical surface. A strut 20 is configured in the base plate 8 between the recesses 18. The common circular-cylindrical surface of the recesses 18 is concentric to a circular-cylindrical space defined by the hollow-cylindrical projection 16. The two recesses 18 penetrate the base plate 8 so that the recesses 18 are connected to the circular-cylindrical space defined by the hollow-cylindrical projection 16. The circular-cylindrical space defined by the hollow-cylindrical projection 16 forms a sensor accommodation 22, the top of which is partially accessible from above due to the recesses 18. The strut 20 forms a stop for a sensor (not shown) received in the sensor accommodation 22 and/or provides a stiffening (strength increase) of the base 6 or of the base plate 8, respectively.

At each of the two acute-angled corners of the rhombus-shaped base plate 8, a circular-cylindrical fixing recess 24 is configured that is oriented perpendicular to the plane of extension of the base plate 8 or, respectively, runs parallel to the projection 16. The fixing recesses 24 are configured to be able to fix the anchoring device 2, for example, via screws or clips (not shown) to a housing of a medical device or to a fixation bandage of a person to be treated or monitored.

At one of the two acute-angled corners of the rhombus-shaped base plate 8, a bow-shaped projection 26 is provided, which is configured in such a way that an identification tape or a security seal for the anchoring device 2 can be attached to the projection 26. Alternatively or additionally, the bow-shaped projection 26 may be arranged and/or configured such that a (new or further) anchoring point for the line 64 to the anchoring device 2 and/or an anchoring point for the anchoring device 2 to a medical device may be created at the bow-shaped projection 26 with a cable tie or the like.

At the obtuse-angled corner of the rhombus-shaped base plate 8 at which the middle pin 12 is located, a cover hinge 28 is configured at a lower rim of the base plate 8.

The cover 4 is pivotably connected to the base 6 or to the base plate 8 via the cover hinge 28.

The cover 4 has a receptacle part 30 with a receptacle portion 32 and a second receptacle portion 34. The receptacle part 30 is connected to the cover hinge 28. A coupling portion 38 is pivotably connected to the receptacle part 30 via a coupling portion hinge 36.

The cover 4 is configured in the shape of a band, so that the receptacle part 30 corresponds essentially to a rectangular plate, on the two short sides of which on the one hand the cover hinge 28 and on the other hand the coupling portion hinge 36 are arranged.

The coupling portion 38 also corresponds substantially to a rectangular plate, which is connected to the receptacle part 30 on one side via the coupling portion hinge 36. At the two free corners of the rectangular plate-shaped coupling portion 38, coupling pins 40 and 42 are configured, which are oriented perpendicular to a plane of extension of the coupling portion 38, i.e.

upward in the opened position of the cover 4. The coupling pins 40 and 42 are configured to hold the cover 4 in position in the closed state and to prevent or complicate slipping of the cover 4 relative to the base 6 or to the base plate 8, respectively. The cover 4 cannot detach upward due to a flexible tongue 52 or a snap hook, respectively.

Figures 4, 5:
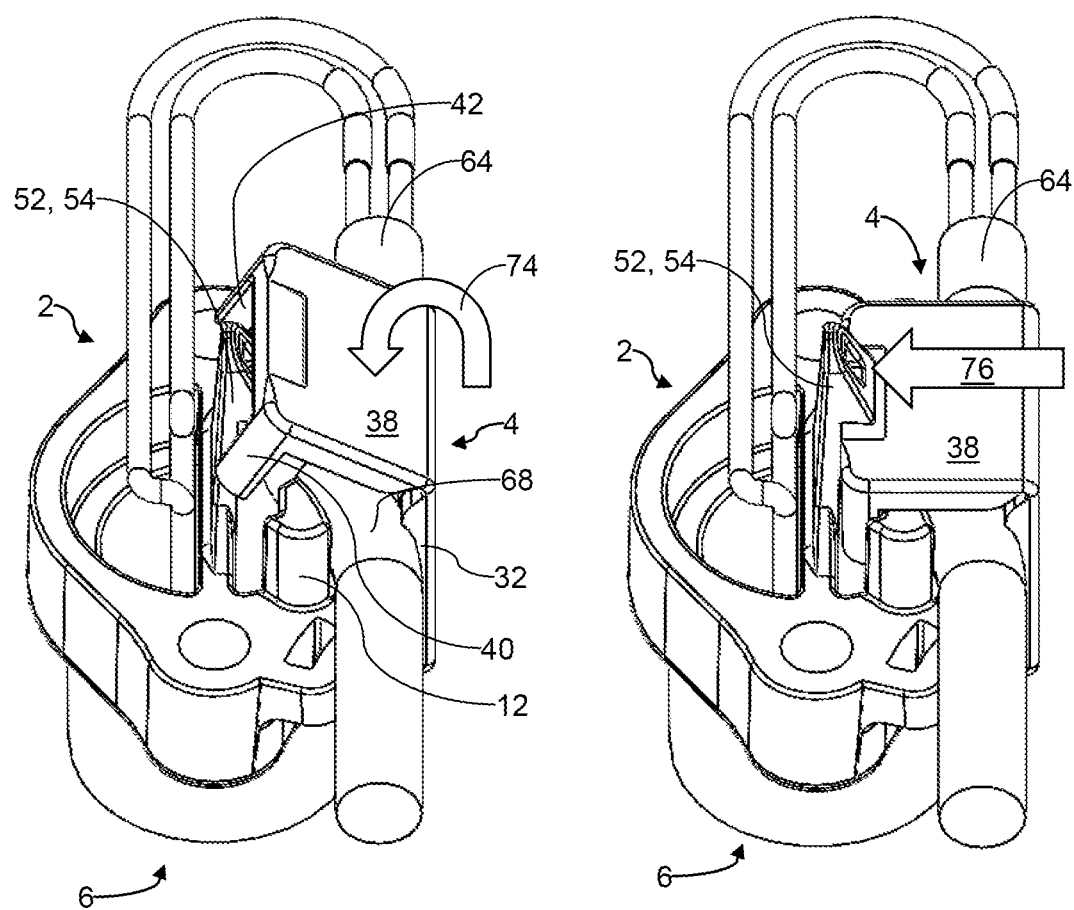
FIG. 4 shows a perspective view of the system shown in FIG. 3 in a state in which the cover of the anchoring device is pivoted from the opened position in the direction of a closed position.
FIG. 5 shows a perspective view of the system shown in FIG. 4 in a state in which the cover of the anchoring device is in the closed position.

The outer pins 12 and 14 of the base 6 are configured such that they each have an outer surface or contact surface 44 or 46, which can come into surface contact with a corresponding outer surface or contact surface 48 or 50 of the corresponding coupling pin 40 or 42, respectively, when the cover 4 is in a closed position relative to the base 6 (see FIG. 5).

The flexible tongue 52 extends upward from the strut 20 of the base plate 8. The flexible tongue 52 is oriented substantially parallel to the pins 10, 12 and 14. The flexible tongue 52 and the pins 10, 12 and 14 are arranged in a rhombus in such a way that the flexible tongue 52 and the middle pin 10 are arranged at the obtuse-angled corners of the rhombus and the two outer pins 12 and 14 are arranged at the acute-angled corners of the rhombus. At the free end, the flexible tongue 52 has a wedge-shaped hook 54.

Between the middle pin 10 and the outer pin 12 or 14, the base plate 8 is configured in an arcuate shape, so that a gap 56 between the middle pin 10 and the outer pin 12 and a gap 58 between the middle pin 10 and the outer pin 14 together define an indentation 60 which is at least sectionally channel-shaped. Due to the arrangement of the pins 10, 12 and 14 in a triangle, the indentation 60, which is at least sectionally channel-shaped, is curvilinear or the indentation 60, which is at least sectionally channel-shaped, has a kink. The flexible tongue 52 is configured wider than the pins 10, 12 and/or 14, so that gaps 62 between the flexible tongue 52 and the respective outer pin 12 or 14 are smaller than the gap 56 or 58.

Figure 2:
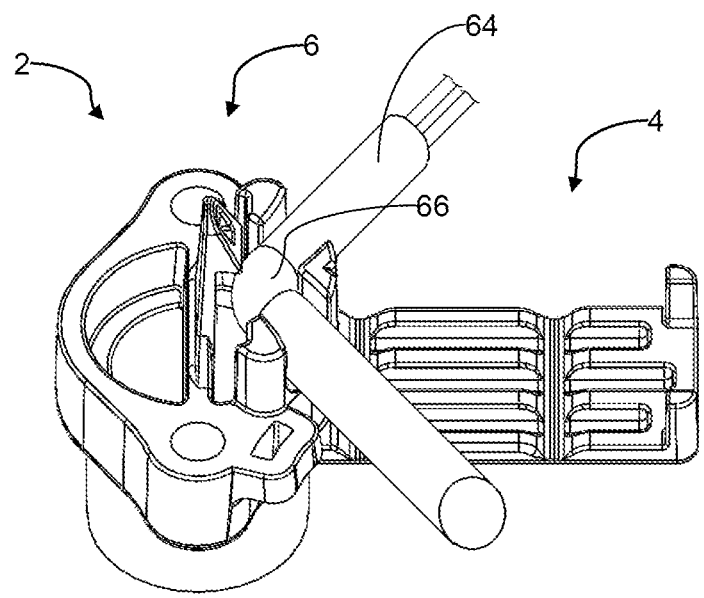
FIG. 2 shows a perspective view of a system according to the disclosure in a state in which a line curved at a first site is inserted into the opened anchoring device according to FIG. 1.

FIG. 2 shows a perspective view of a system according to the disclosure in a state in which the anchoring device 2 is open or the cover 4 is in the opened position relative to the base 6, and a line 64 is inserted into the indentation 60.

Due to the triangular arrangement of the pins 10, 12 and 14 or due to the curvilinear form of the indentation 60, the inserted line 64 is curved at a first site 66 or in a first portion, respectively. This curvature already ensures a certain self-locking effect, due to which sliding out of the line 64 out of the indentation 60 in the extension direction of the indentation 60 is prevented or made more difficult.

In the state shown in FIG. 2, the line 64 extends from the two spaces 56 and 58 or from the two ends of the indentation 60, respectively, in alignment with the two spaces 56 and 58.

Figure 3:
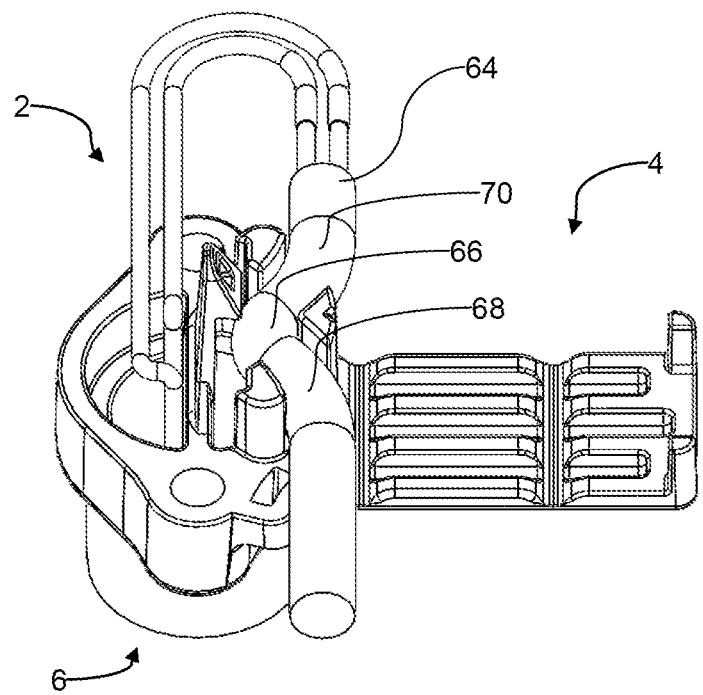
FIG. 3 shows a perspective view of the system shown in FIG. 2 in a state in which the line inserted in the anchoring device is additionally curved at a second site and at a third site.

In the state shown in FIG. 3, the line 64 is curved in a region adjacent to the gap 56 at a second site 68 or in a second portion, and in a region adjacent to the gap 58 at a third site 70 or in a third portion. Since the line 64 is curved not only at the first site 66, but additionally at the second site 68 and at the third site 70, the self-locking effect caused by the curvature only at the first site 66 can be supported. The curvatures at the second site 68 and at the third site 70 are opposite to the curvature at the first site 66 and are according to amount such that the portions of the line 64 adjacent to the second site 68 and at the third site 70 and projecting from the anchoring device 2 are collinear. In the state shown in FIG. 3, the line 64 is already curved at the three sites 66, 68 and 70. In particular, the anchoring device 2 is configured in such a way that the curvatures at the second and third sites 68 or 70, respectively, can be caused by closing the cover 4.

In order to curve the line 64 at the second site 68 and at the third site 70, receptacle portions 32 and 34 are provided on the receptacle part 30 of the cover 4.

FIG. 4 shows a perspective view of the system shown in FIG. 3 in a state in which the cover 4 of the anchoring device 2 is pivoted from the opened position toward the closed position. In the state shown in FIG. 4, the receptacle part 30 is pivoted to the base plate 8 such that the receptacle portion 32 ensures the curvature of the line 64 at the second site 68, the second receptacle portion 34 ensures the curvature of the line 64 at the third site 70, a portion 72 of the receptacle part 30, which is arranged between the receptacle portion 32 and the second receptacle portion 34 (see FIG. 1), abuts an outer side or surface of the middle pin 10, and the free end of the coupling portion 38 opposite the coupling portion hinge 36 rests on the wedge-shaped hook 54 of the flexible tongue 52.

If the cover 4 or the coupling portion 38 is pivoted from the position shown in FIG. 4 further in the direction of the base 6 (see arrow 74 in FIG. 4), the coupling pins 40 and 42 move toward the corresponding pins 12 and 14 of the base 6 and engage behind the pins 12 and 14 in such a way that pivoting of the receptacle part 34 away from the base 6 is prevented by interaction of the coupling pins 40 and 42 with the pins 12 and 14 of the base 6 or by interaction of the contact surfaces 48, 50 on the side of the cover 4 with the corresponding contact surfaces 44 and 46 on the side of the base 6. During the pivoting of the coupling portion 38 and the resulting engagement of the pins 12 and 14 by the coupling pins 40 and 42, an interaction of the free end of the coupling portion 38 with an inclined surface of the wedge-shaped hook 54 causes a deflection of the flexible tongue 52 in the direction away from the middle pin 10. When the coupling portion 38 is pivoted in such a way that the coupling pins 40 and 42 and the pins 12 and 14 are oriented parallel to each other and the contact surfaces 48 and 50 of the coupling pins 40 and 42 rest on the contact surfaces 44 and 46 of the pins 12 and 14, the flexible tongue 52 snaps shut in such a way that the wedge-shaped hook 54 engages form-fittingly around or behind the free end of the coupling portion 38. In this position of the coupling portion 38, the cover 4 is in the closed position, which is shown in FIG. 5.

In the state shown in FIG. 5, sliding out of the line 64 out of the indentation 60 in the direction transverse to the extension direction of the indentation 60 is prevented or made more difficult by the coupling portion 38, and in the direction of the extension direction of the indentation 60 is prevented or made more difficult by the self-locking effect caused by the indentation 60 and the receptacle portions 32 and 34.

In order to remove the line 64 of the anchoring device 2, the flexible tongue 52 has to be pivoted away from the coupling portion 38 (see arrow 76 in FIG. 5) in such a way that the hook 54 no longer interacts form-fittingly with the free end of the coupling portion 38 and the coupling portion 38 can be pivoted away from the base 6.

The anchoring device 2 according to FIGS. 1 to 5 is uniformly made of a thermoplastic material.

The invention claimed is:

1. An anchoring device for anchoring a line, the anchoring device comprising:
   a base having an indentation configured to receive a portion of the line in the indentation and defining a curvilinear cavity curved at a first site in a first direction to prevent or limit, in a self-locking manner, said portion of the line from sliding out of the indentation in an extension direction of the indentation; and
   a cover which, in an open position, releases the indentation for insertion of the line and, in a closed position, covers the indentation to prevent or limit said portion of the line from sliding out of the indentation transversely to the extension direction of the indentation,
   the cover comprising a receptacle portion which, in the closed position of the cover, is arranged at one end of the indentation and extends the curvilinear cavity in such a way that the curvilinear cavity is curved in a region of the receptacle portion at a second site in a second direction running transversely or in an opposite direction to the first direction
   wherein:
      the receptacle portion extends from a first receptacle portion end to a second receptacle portion end, wherein the first receptacle portion end is directly pivotally connected to the base to rotate about a first pivot axis, and
      the cover further comprises a coupling portion that extends from a first coupling portion end to a second coupling portion end, wherein the first coupling portion end is directly pivotally connected to the second receptacle portion end to rotate about a second pivot axis, and wherein the second coupling portion end is configured to be selectively secured to the base with the coupling portion covering the indentation.

2. The anchoring device according to claim 1, wherein the cover comprises a second receptacle portion arranged at a second end of the indentation in the closed position of the cover, the second receptacle portion extending the curvilinear cavity such that the curvilinear cavity is curved in a region of the second receptacle portion at a third site in a third direction extending transversely or opposite to the first direction.

3. The anchoring device according to claim 2, wherein the second direction and third direction are parallel.

4. The anchoring device according to claim 1, wherein the base comprises a base plate and three pins extending from the base plate, and the indentation is formed by two spaces extending between the pins.

5. The anchoring device according to claim 4, wherein the cover is configured such that, in the closed position of the cover, at least a part of the cover abuts at least one of the pins.

6. The anchoring device according to claim 1, wherein the coupling portion is configured to be coupled to the base to be releasable without tools in the closed position of the cover and to prevent or limit said portion of the line from sliding out of the indentation transversely to the extension direction of the indentation.

7. The anchoring device according to claim 6, wherein the base and the cover are integrally configured, the first receptacle portion end is directly pivotally connected to the base by a cover hinge, the first coupling portion end is directly pivotally connected to the second receptacle portion end by a coupling portion hinge, and the cover hinge and the coupling portion hinge are film hinges.

8. The anchoring device according to claim 1, wherein the base comprises a sensor accommodation.

9. A system comprising:
an anchoring device according to claim 1; and
the line.

10. The anchoring device of claim 1, wherein the first pivot axis is parallel to the second pivot axis.

11. The anchoring device according to claim 1, wherein the base comprises a hook configured to capture the second coupling portion end when the cover is in the closed position.

12. The anchoring device according to claim 1, wherein the cover is movable to an intermediate position in which:
the receptacle portion is arranged at the one end of the indentation and extends the curvilinear cavity in such a way that the curvilinear cavity is curved in a region of the receptacle portion at the second site in the second direction running transversely or in the opposite direction to the first direction; and
the coupling portion extends parallel to the receptacle portion without covering the indentation to thereby not prevent or limit said portion of the line from sliding out of the indentation transversely to the extension direction of the indentation.

\* \* \* \* \*